United States Patent [19]
Sabatucci et al.

[11] Patent Number: 4,810,699
[45] Date of Patent: Mar. 7, 1989

[54] SUBSTITUTED 1,3,4,9-TETRAHYDROPYRANO[3,4,-B]INDOLE-1-ACETIC ACIDS, PHARMACEUTICAL COMPOSITIONS CONTAINING THEM, AND METHODS FOR TREATING INFLAMMATORY CONDITIONS AND FOR ANALGESIC PURPOSES USING THEM

[75] Inventors: Joseph P. Sabatucci; Christopher A. Demerson, both of Plainsboro; Amadeo A. Failli, Princeton Junction, all of N.J.

[73] Assignee: American Home Products Corporation, New York, N.Y.

[21] Appl. No.: 99,025

[22] Filed: Sep. 21, 1987

[30] Foreign Application Priority Data

Feb. 20, 1987 [CA] Canada ................................ 530246

[51] Int. Cl.$^4$ ..................... A61K 31/40; C07D 491/52
[52] U.S. Cl. .................................... 514/161; 514/282; 514/411; 548/432
[58] Field of Search ................ 548/432; 514/411, 282, 514/161

[56] References Cited

U.S. PATENT DOCUMENTS

| | | | |
|---|---|---|---|
| 3,843,681 | 10/1974 | Demerson et al. | 548/432 |
| 3,939,178 | 2/1976 | Demerson et al. | 548/432 |
| 3,974,179 | 8/1976 | Demerson et al. | 548/432 |
| 4,012,417 | 3/1977 | Demerson et al. | 548/432 |
| 4,585,877 | 4/1986 | Demerson et al. | 548/432 |
| 4,670,462 | 6/1987 | Katz et al. | 514/411 |
| 4,686,213 | 8/1987 | Ferdinandi et al. | 514/411 |

OTHER PUBLICATIONS

Demerson et al., Journal of Medicinal Chemistry, vol. 19, No. 3, pp. 391–395 (1976).
McOmie, "Protective Groups in Organic Chemistry", Plenum Press, london & New York, 1973, p. 149.
Greene, "Protective Groups in Organic Synthesis", John Wiley & Sons, New York, 1981, p. 95.

Primary Examiner—Nicholas S. Rizzo
Assistant Examiner—Diana G. Rivers
Attorney, Agent, or Firm—Walter Patton

[57] ABSTRACT

Indole derivatives characterized by having a 1,3,4,9-tetrahydropyrano[3,4-b]indole-1-acetic acid nucleus bearing a substituent in position 1,5, 6, 7 and 8. The derivatives are useful anti-inflammatory and analgesic agents and methods for their preparation and use are also disclosed.

8 Claims, No Drawings

SUBSTITUTED 1,3,4,9-TETRAHYDROPYRANO[3,4,-B]INDOLE-1-ACETIC ACIDS, PHARMACEUTICAL COMPOSITIONS CONTAINING THEM, AND METHODS FOR TREATING INFLAMMATORY CONDITIONS AND FOR ANALGESIC PURPOSES USING THEM

BACKGROUND OF THE INVENTION a. Field of Invention

This invention relates to novel indole derivatives, and to the processes for their preparation and use.

Notwithstanding the advances made during the last four decades in the development of agents for the treatment of inflammatory conditions and for analgesic purposes in conditions which require relief from pain in a mammal, there still remains a need for effective agents without the side effects associated with the therapeutic agents presently used for these purposes.

More specifically, this invention relates to tricyclic acetic acid derivatives in which the tricyclic portion thereof is characterized by having an indole portion fused to a pyrano ring. Still more specifically, the compounds of this invention are characterized as derivatives of the following tricyclic acetic acid system:

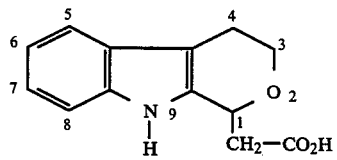

1,3,4,9-tetrahydropyrano[3,4-b]indole-1-acetic acid in which the carbons at the 1-, 5-, 6-, 7-, and 8-positions are further substituted.

The indole derivatives of this invention have been found to exhibit useful pharmacodynamic properties without eliciting undesirable side effects. Notable attributes of this effect are anti-inflammatory and analgesic activities.

b. Prior Art

The closest prior art to the present invention is:

Demerson et al, U.S. Pat. No. 3,939,178. Demerson et al disclosed 1,3,4,9-tetrahydropyrano[3,4-b]indoles and 1,3,4,9-tetrahydrothiopyrano[3,4-b]indoles having analgesic and anti-inflammatory activity but not with the substituents of the present invention. Related U.S. patents are U.S. Pat. Nos. 3,974,179 and 3,843,681. Also relevant is U.S. Pat. No. 4,670,462, June 2, 1987.

SUMMARY OF THE INVENTION

The compounds of this invention are represented by formula (I)

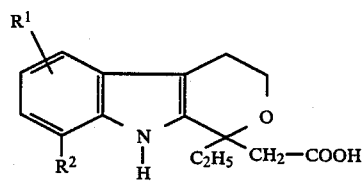

wherein $R^1$ is hydrogen, lower alkyl containing 1 to 4 carbon atoms or halogen, $R^2$ is —O CH$_2$—CH=CH$_2$, —O—CH$_2$—CF$_3$, —O—CH(CH$_3$)—CF$_3$, —O—CH$_2$—C≡CH and the pharmaceutically acceptable salts thereof.

A preferred aspect of the present invention is the series of compounds represented by formula (I) wherein $R^1$ is hydrogen or chlorine, $R^2$ is —O—CH$_2$—CF$_3$ and the pharmaceutically acceptable salts thereof.

The most preferred compounds of the present invention are designated 7-chloro-1-ethyl-1,3,4,9-tetrahydro-8-(2,2,2-trifluoroethoxy)-pyrano[3,4-b]indole-1-acetic acid;

1-ethyl-1,3,4,9-tetrahydro-8-(2,2,2-trifluoroethoxy)-pyrano[3,4-b]indole-1-acetic acid;

1-ethyl-1,3,4,9-tetrahydro-5-methyl-8-(2,2,2-trifluoroethoxy)-pyrano[3,4-b]indole-1-acetic acid;

1-ethyl-5-fluoro-1,3,4,9-tetrahydro-8-(2,2,2-trifluoroethoxy)-pyrano[3,4-b]indole-1-acetic acid;

7-fluoro-1-ethyl-1,3,4,9-tetrahydro-8-(2,2,2-trifluoroethoxy)-pyrano[3,4-b]indole-1-acetic acid;

7-chloro-1-ethyl-1,3,4,9-tetrahydro-8-(1-methyl-2,2,2-trifluoroethoxy)-pyrano[3,4-b]indole-1-acetic acid;

1-ethyl-1,3,4,9-tetrahydro-8-[(2-propenyl)oxy]-pyrano[3,4-b]indole-1-acetic acid; and 1-ethyl-1,3,4,9-tetrahydro-8-[(2-propynyl)oxy]-pyrano[3,4-b]indole-1-acetic acid.

The indole derivatives of this invention of formula (I) are prepared by the following processes.

Process 1

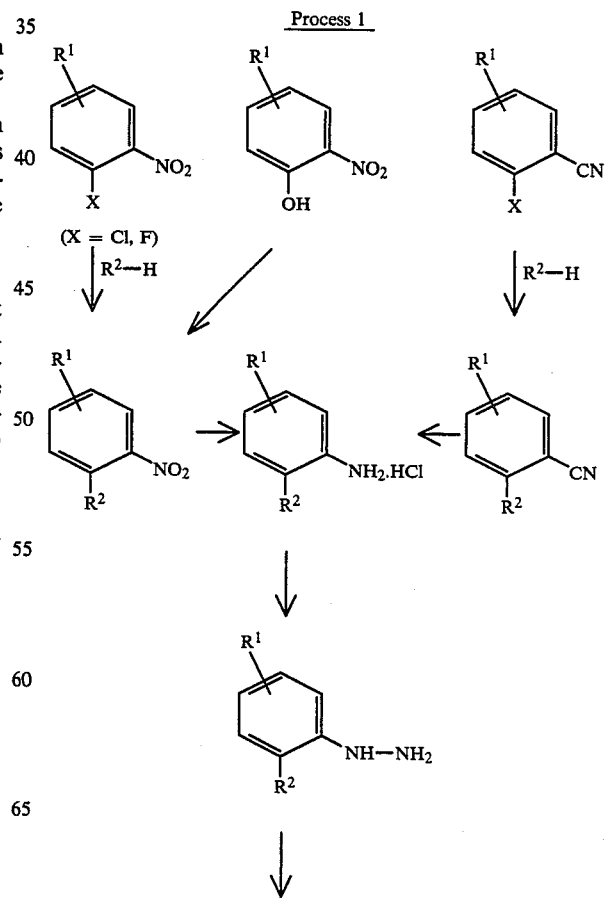

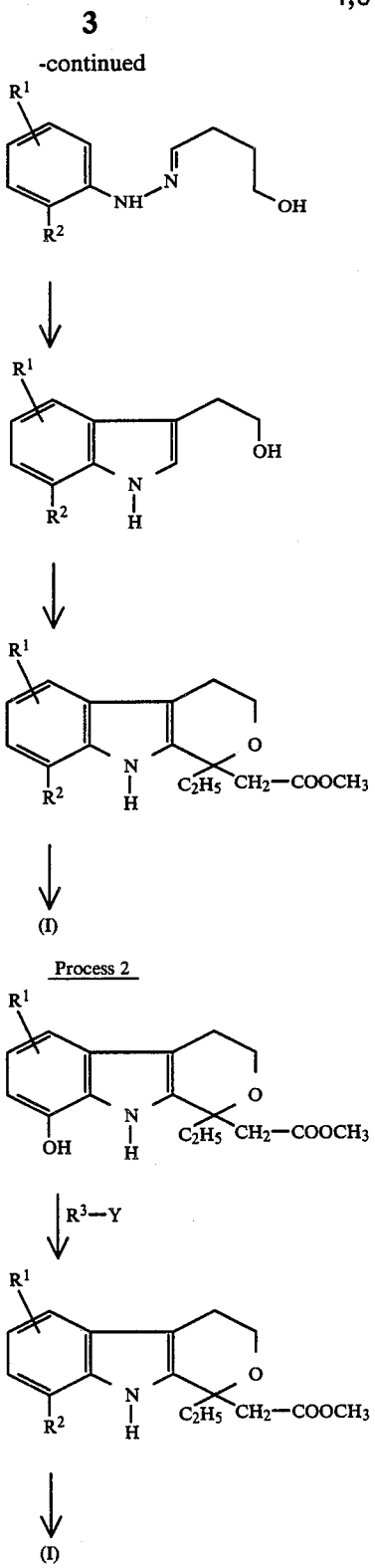

wherein $R^1$ and $R^2$ are as defined above, $R^3$ is $-CH_2CH=CH_2$, $-CH_2-CF_3$, $-CH(CH_3)-CF_3$, or $-CH_2-C\equiv CH$ and Y is bromine or iodine.

DETAILED DESCRIPTION OF THE INVENTION

The term "lower alkyl" as used herein represents straight chain alkyl radicals containing 1 to 4 carbon atoms and branched chain alkyl radicals containing three to four carbo atoms and includes methyl, ethyl, propyl, isopropyl, butyl, isobutyl and the like.

The term "halogen" as used herein includes fluorine, chlorine, bromine and iodine.

The compounds of formula (I) form salts with suitable pharmaceutically acceptable inorganic and organic bases. These derived salts possess the same activities as the parent acid and are included within the scope of this invention. The acid of formula (I) is transformed in excellent yield into the corresponding pharmaceutically acceptable salts by neutralization of said acid with the appropriate inorganic or organic base. The salts are administered in the same manner as the parent acid compounds. Suitable inorganic bases to form these salts include, for example, the hydroxides, carbonates, bicarbonates or alkoxides of the alkali metals or alkaline earth metals, for example, sodium, potassium, magnesium, calcium and the like. Suitable organic bases include the following amines; lower mono-, di- and trialkylamines, the alkyl radicals of which contain up to three carbon atoms, such as methylamine, dimethylamine, trimethylamine, ethylamine, di- and triethylamine, methylethylamine, and the like; mono, di- and trialkanolamines, the alkanol radicals of which contain up to three carbon atoms, such as mono-, di- and triethanolamine; alkylenediamines which contain up to six carbon atoms, such as hexamethylenediamine; amino sugars, such as glucosamine; cyclic saturated or unsaturated bases containing up to six carbon atoms, such as pyrrolidine, piperidine, morpholine, piperazine and their N-alkyl and N-hydroxyalkyl derivatives, such as N-methylmorpholine and N-(2-hydroxyethyl)piperidine, as well as pyridine. Furthermore, there may be mentioned the corresponding quaternary salts, such as the tetraalkyl (for example tetramethyl), alkyl-alkanol (for example methyltrimethanol and trimethyl-monoethanol) and cyclic ammmonium salts, for example the N-methyl-pyridinium, N-methyl-N-(2-hydroxyethyl)-morpholinium, N,N-dimethyl-morpholinium, N-methyl-N-(2-hydroxyethyl)-morpholinium, N,N-dimethyl-piperidinium salts, which are characterized by good water-solubility. In principle, however, there can be used all the ammonium salts which are physiologically compatible.

The transformations to the salts can be carried out by a variety of methods known in the art. For example, in the case of salts of inorganic bases, it is preferred to dissolve the acid of formula (I) in water containing at least one equivalent amount of a hydroxide, carbonate, or bicarbonate. Advantageously, the reaction is performed in a water-miscible organic solvent inert to the reaction conditions, for example, methanol, ethanol, dioxane, and the like in the presence of water. For example, such use of sodium hydroxide, sodium carbonate or sodium bicarbonate gives a solution of the sodium salt. Evaporation of the solution or additio of a water-miscible solvent of a more moderate polarity, for example, a lower alkanol, for instance, butanol, or a lower alkanone, for instance, ethyl methyl ketone, gives the solid salt if that form is desired.

To produce an amine salt, the acid of formula (I) is dissolved in a suitable solvent of either moderate or low polarity, for example, ethanol, acetone, ethyl acetate, diethyl ether and benzene. At least an equivalent amount of the amine corresponding to the desired cation is then added to that solution. If the resulting salt does not precipitate, it can usually be obtained in solid form by addition of a miscible diluent of low polarity, for example, benzene or petroleum ether, or by evaporation. If the amine is relatively volatile, any excess can easily by removed by evaporation. It is preferred to use substantially equivalent amounts of the less volatile amines.

Salts wherein the cation is quaternary ammonium are produced by mixing the acid of formula (I) with an equivalent amount of the corresponding quaternary ammonium hydroxide in water solution, followed by evaporation of the water.

Also included in this invention are the optical isomers of the compounds of formula (I) which result from asymmetric centers, contained therein i.e. 1-carbon. Such isomers can be obtained in substantially pure form by classical separation techniques and by sterically controlled synthesis. Included is the specific case of the resolution of 1-ethyl-1,3,4,9-tetrahydro-pyrano[3,4-b]indole-1-acetic acids into their optical isomers by separation of the corresponding [(1S)-endo]-1,7,7-trimethyl-bicyclo[2.2.1]heptan-2-yl ester followed by basic hydrolysis.

ANTI-INFLAMMATORY ACTIVITY

The useful anti-inflammatory activities of the pyranoindole acetic acid derivatives of formula (I) are demonstrated in standard pharmacologic tests, for example, the test designated: Preventative Adjuvant Edema The objective of this test is to determine the ability of test drugs to exhibit an acute anti-inflammatory effect in rats. This test is a primary screen for anti-inflammatory drugs.

Species:

Male Sprague Dawley rats (180-200 g) are used. The animals have free access to water but food is withdrawn 18 hours before testing.

Drug Preparations and Administration:

Freund's complete adjuvant is prepared by suspending 5 mg of killed and dried *Mycobacterium butyricum* (Difco) in 1 mL mineral oil. The test compound are dissolved, or suspended in 0.5% Tween 80 in distilled water according to their solubility. For primary screening all drugs are administered by gastric lavage at the arbitrary dosage of 25 mg/kg, p.o. in a volume of 0.5 mL/100 g body weight to groups of 10 animals.

Methodological Details:

The method is essentially that described by Wax et al, J. Pharmacol. Exp. Ther., 192, 166-171 (1975). Groups of rats are injected intradermally in the left hind paw with 0.1 mL of Freund's complete adjuvant. The test compound or vehicle is administered immediately before the adjuvant, 24 hours and 48 hours after the adjuvant (days 0, 1 and 2). The injected hind paw volume is measured before the injection of adjuvant and 24 hrs. after the last drug administration (day 3) by means of a plethysmometer (Buxco Electronics Inc.). The difference between the hind paw volume on day 0 and day 3 represents the edema volume. Etodolac (25 mg/kg, p.o.) is included as a positive control.

Presentation of Results:

The mean edema volume (expressed as mL±SEM) is calculated for each group and the percentage protection conferred by the drug is calculated:

$$\% \text{ protection} = \frac{(c - t) \, 100}{c}$$

where c is the mean edema volume for the vehicle-treated (0.5% Tween 80 in distilled water) controls and t is the mean edema volume for the drug treated group.

ANALGESIC ACTIVITY

A further test used to determine the utility of the compounds of the present invention is designated: Drug Effects on Phenylbenzoquinone-induced Writhing in Mice The objective of this test is to determine the ability of test drugs to inhibit the nociceptive (pain) response of mice injected with a chemical irritant. This test is a primary screen for both peripheral and centrally acting analgesic drugs.

Species:

Male Swiss albino mice (15-25 g). The animals are fasted for 18 hours prior to use but have free access to water.

Drug Preparation and Administration:

Drugs are dissolved or suspended according to their solubility in 0.5% Tween 80 in distilled water. They are administered by gastric gavage in a volume of 5 mL/kg. For primary screening all drugs are administered at the arbitrary dosage of 25 mg/kg, p.o. to a group of 10 mice.

Methodological Details:

A modification of the method of Siegmund et al, Proc. Soc. Exp. Biol. Med., 95, 729-731 (1957) is used. Groups of 5 mice are dosed with the test compound or vehicle control. Sixty minutes later the animals are injected i.p. with 0.3 mL/20 g body weight of a 0.02% solution of phenylbenzoquinone (PBQ; 2-phenyl-1,4-benzoquinone) and placed in individual observation boxes. The number of writhing or abdominal squirming movements made by each mouse during the following 15 min. period is counted. The experiment is repeated with another group of 5 mice and the mean number of writhes per mouse for a group of 10 mice is calculated.

Presentation of Results:

Drug treated and vehicle-treated control groups are compared and the percentage protection conferred by the drug is calculated:

$$\text{Percentage protection} = \frac{(c - t) \, 100}{c}$$

where c = mean number of writhes in the control group
t = mean number of writhes in the test drug group Typical results obtained for the compounds of the present invention in the aforementioned tests are as follows:

TABLE I

| Substituted 1,3,4,9-Tetrahydropyrano[3,4-b]indole-1-acetic Acids | | |
|---|---|---|
| Example | Preventative Adjuvant Edema* | Phenylquinone Writhing in Mice* |
| 1 | $ED_{50}$ = 16.4 | 34 (10) |
| 2 | 50 (3) | $ED_{50}$ = 77 |
| 3 | 70 (25) | 18 (10) |
| 4 | 83 (10) | 0 (10) |
| 5 | 41 (25) | 31 (10) |
| 6 | $ED_{50}$ = 4.3 | $ED_{50}$ = >200 |
| 7 | 41 (25) | 18 (10) |
| 8 | 34 (25) | — |

*The numbers quoted are either percent inhibition at the dose in mg/kg given in parentheses or the $ED_{50}$.

The lack of side effects associated with the compounds of this invention are demonstrated by standard acute toxicity tests as described by R. A. Turner in "Screening Methods in Pharmacology," Academic Press, New York and London, 1965, pp. 152–163, and by prolonged adminstration of the compound to warm-blooded animals.

When the compounds of this invention are employed as anti-inflammatory and analgesic agents in warm-blooded animals, they are administered orally, alone or in dosage forms, i.e., capsules or tablets, combined with pharmacologically acceptable excipients, such as starch, milk sugar and so forth, or they are administered orally in the form of solutions in suitable vehicles such as vegetable oils or water. The compounds of this invention may be administered orally in sustained release dosage form or transdermally in ointments or patches. The compounds of this invention may also be administered in the form of suppositories.

The dosage of the compounds of formula (I) of this invention will vary with the particular compound chosen and form of administration. Furthermore, it will vary with the particular host under treatment. Generally, the compounds of this inventio are administered at a concentration level that affords efficacy without any deleterious side effects. These effective anti-inflammatory and analgesic concentration levels are usually obtained within a therapeutic range of 1.0 μg to 500 mg/kg per day, with a preferred range of 1.0 μg to 100 mg/kg per day. The preferred anti-inflammatory dose range is 1 μg to 20 mg/kg b.i.d. The preferred analgesic dose range is 1 μg to 4 mg/kg b.i.d.

The compounds of this invention may be administered in conjunction with nonsteroid anti-inflammatory drugs such as acetaminophen, ibuprofen and aspirin and/or with opiate analgesics such as codeine, oxycodone and morphine together with the usual doses of caffeine. When used in combination with other drugs, the dosage of the compounds of the present invention is adjusted accordingly.

The compounds of the present invention also possess antipyretic activity.

The following examples further illustrate this invention.

EXAMPLE 1

1-Ethyl-1,3,4,9-tetrahydro-5-methyl-8-(2,2,2-trifluoroethoxy)pyrano[3,4-b]indole-1-acetic Acid (I, $R^1$=5—CH$_3$, $R^2$=8—O—CH$_2$CF$_3$)

Step 1. Preparation of 5-Methyl-2-(2,2,2-trifluoroethoxy)aniline Hydrochloride 2,2,2-Trifluoroethanol (60 g, 0.6 mol) was added dropwise to a stirred mixture of sodium hydride (12 g of a 60% dispersion, 0.3 mol) in 500 mL of DMF. After stirring for 20 minutes, 4-chloro-3-nitrotoluene (51.3 g, 0.3 mol) was added and the reaction heated at 150° C. for 16 hours. The reaction was cooled, poured into ice cold 5% HCl. The resulting precipitate was collected by filtration, dried to give 64 g of 5-methyl-2-(2,2,2-trifluoroethoxy)nitrobenzene.

$^1$H NMR (CDCl$_3$): δ 8.4 (bs, 1H), 7.7 (s, H$_{arom}$), 7.4 (d, H$_{arom}$, J=8 Hz), 7.03 (d, H$_{arom}$, J=8 Hz), 4.48 (q, 2H, J=8 Hz), 2.4 (s, 3H)

Hydrogenation in a Parr bomb in 600 mL of ethanol containing 2.8 g of 10% palladium on charcoal afforded, after filtration and treatment with ethereal HCl, 58 g (80%) of 5-methyl-2-(2,2,2-trifluoroethoxy)aniline hydrochloride, m.p. 223°–225° C.

Step 2. Preparation of 5-Methyl-2-(2,2,2-trifluoroethoxy)phenylhydrazine Hydrochloride Sodium nitrite (18.3 g, 0.265 mol) in 40 mL water was added dropwise to a cold stirred mixture of 5-methyl-2-(2,2,2-trifluoroethoxy)aniline hydrochloride (58.0 g, 0.24 mol) concentrated HCl (94 mL) and water (95 mL) so that the temperature remained at −5° to −3° C. After the addition was complete, a solution of stannous chloride dihydrate (108.3 g, 0.48 mol) in 214 mL, 6N HCl was added over a 1 hour period keeping the temperature below 0° C. After the addition was complete stirring was continued for 1 hour and then for 20 hours at room temperature. The reaction was then cooled in an ice bath and made alkaline (pH 10–11) by the addition of 50% NaOH. The resulting solution was extracted with ethyl acetate (3×). The combined extracts were washed with water, dried (MgSO$_4$) and concentrated to afford a solid hydrazine. This was dissolved in ether and ethereal HCl added. The precipitated 5-methyl-2-(2,2,2-trifluoroethoxy)phenylhydrazine hydrochloride was collected (47 g) (76%).

Step 3. Prepation of 4-Methyl-7-(2,2,2-trifluoroethoxy)tryptophol 2,3-Dihydrofuran (27 g, 0.38 mol) was added over a 20 minute period to a stirred solution of 5-methyl-2-(2,2,2-trifluoroethoxy)phenylhydrazine hydrochloride (47 g, 0.183 mol), 200 mL dioxane and 14 mL water. The internal temperature was then increased to 90°–95° C. for 3.5 hours. The reaction was cooled and poured into ether (2 L), dried and concentrated to give 53 g of crude product. Chromatography using 40% EtOAc/hexane afforded 9.8 g (20%) of 4-methyl-7-(2,2,2-trifluoroethoxy)tryptophol.

$^1$H NMR (CDCl$_3$): δ 7.02 (d, 1H$_{arom}$, J=2.5 Hz), 6.76 (d, 1H$_{arom}$, J=8 Hz), 6.5 (d, 1H$_{arom}$, J=8 Hz), 4.45 (q, 2H, J=8 Hz), 3.88 (t, 2H, J=5 Hz), 3.18 (t, 2H, J=5 Hz), 2.62 (s, 3H)

Step 4. Preparation of 1-Ethyl-1,3,4,9-tetrahydro-5-methyl-8-(2,2,2-trifluoroethoxy)-pyrano[3,4-b]indole-1-acetic Acid A mixture consisting of 4-methyl-7-(2,2,2-trifluoroethoxy)tryptophol (9.8 g, 0.036 mol), methyl 3-methoxy-2-pentenoate (5.0 g, 0.035 mol), CH$_2$Cl$_2$ (400 mL) and BF$_3$.Et$_2$O (1 mL) was stirred at room temperature for 3 hours, washed with 5% NaHCO$_3$, water, dried (MgSO$_4$) and concentrated to afford 12 g of crude 1-ethyl-1,3,4,9-tetrahydro-5-methyl-8-(2,2,2-trifluoroethoxy)-pyrano[3,4-b]indole-1-acetic acid, methyl ester. Flash chromatography using 13% EtOAc-hexane gave 7.2 g of solid ester, mp 138°–140° C. The above ester was hydrolyzed in 400 mL MeOH containing 7.0 g KOH and 10 mL water by refluxing for 4 hours. The reaction solution was concentrated, diluted with water and extracted with ether (2×200 mL). The aqueous phase was acidified with 6N HCl and extracted with chloroform (2×200 mL). The combined chloroform extracts were washed with water, dried (MgSO$_4$) and concentrated to afford 6.4 g of solid 1-ethyl-1,3,4,9-tetrahydro-5-methyl-8-(2,2,2-trifluoroethoxy)-pyrano[3,4-b]indole-1-acetic acid. Recrystallization from toluene-petroleum ether afforded 5.0 g (37%) of pure product, m.p. 149°–151° C.

EXAMPLE 2

7-Chloro-1-ethyl-1,3,4,9-tetrahydro-8-(2,2,2-trifluoroethoxy)pyrano[3,4-b]indole-1-acetic Acid (I, $R^1$=7—Cl, $R^2$=8—O—$CH_2$—$CF_3$)

Step 1. Preparation of 3-Chloro-2-(2,2,2-trifluoroethoxy)nitrobenzene

According to the procedure of J. T. Gupton et al, Can. J. Chem. 63, 3037 (1985), a suspension of hexane-washed sodium hydride (8.4 g, 0.21 mol) in DMF (250 mL) was added to 2,2,2-trifluoroethanol (22.1 mL, 0.3 mol) dropwise in 200 mL of DMF at room temperature over 60 minutes (excessive frothing occurs if added too fast). After stirring an additional 30 minutes 2,3-dichloronitrobenzene (38 g, 0.20 mol) was added in one portion. The resulting mixture was stirred at room temperature for 2 hours. The reaction was then poured into 1N HCl (500 mL) and extracted with $Et_2O$ (2×500 mL). The combined $Et_2O$ layers were washed first with water (200 mL) and finally with saturated brine (200 mL). After drying ($MgSO_4$), the ether was concentrated to yield 47 g (90% based on dichloronitrobenzene) of 3-chloro-2-(2,2,2-trifluoroethoxy)nitrobenzene as a yellow liquid (b.p. 85° C./0.3 mmHg), which was used without further purification.

Step 2. Preparation of 3-Chloro-2-(2,2,2-trifluoroethoxy)aniline Hydrochloride 3-Chloro-2-(2,2,2-trifluoroethoxy)nitrobenzene (47 g, 185 mmol) and tin chloride dihydrate (126.5 g, 555 mmol) were placed in a 3 neck flask equipped with an overhead stirrer. Concentrated HCl (231 mL) was added in one portion with rapid stirring, and the reaction heated rapidly until it was homogeneous. After stirring an additional 15 minutes, the mixture was cooled to 0° C. and 50% NaOH added to pH=13. The alkaline solution was extracted with $Et_2O$ (2×500 mL) and the combined $Et_2O$ layers were washed with brine (2×500 mL), dried ($MgSO_4$), and concentrated to afford 35 g of 3-chloro-2-(2,2,2-trifluoroethoxy)aniline as a light yellow oil. This oil was dissolve in the minimum amount of ether (~100 mL), then saturated with HCl gas. The product was precipitated by the addition of hexane (250 mL), and the resulting solid removed by filtration to afford 31 g (65%) of 3-chloro-2-(2,2,2-trifluoroethoxy)aniline as the hydrochloride salt, m.p. 170°–180° C. (dec.).

Step 3. Preparation of 3-Chloro-2-(2,2,2-trifluoroethoxy)phenylhydrazine Hydrochloride A mixture of 3-chloro-2-(2,2,2-trifluoroethoxy)aniline hydrochloride (20 g, 77 mmol), concentrated HCl (50 mL), and $H_2O$ (30 mL) was cooled to −10° C. Sodium nitrite (10.7 g, 155 mmol) dissolved in $H_2O$ (30 mL) was added dropwise at a rate to maintain the temperature below −5° C. The solution was stirred for an additional 30 minutes. At the end of this time $SnCl_2.2H_2O$ (65 g, 289 mmol) in 125 mL of 6N HCl was added dropwise over 1 hour at 0° C. When addition was complete the mixture was allowed to warm to room temperature and stirred an additional 18 hours. The reaction was cooled to −5° C. and 50% NaOH solution was added slowly to pH=13. This alkaline solution was extracted with EtOAc (3×500 mL), and the combined organic layers were washed with brine (2×500 mL), dried ($MgSO_4$), and concentrated to yield an orange oil. This residue was dissolved in 100 mL $Et_2O$ and saturated with HCl gas, which resulted in a turbid solution. After the addition of hexane (~10 volumes) and cooling, the 3-chloro-2-(2,2,2-trifluoroethoxy)phenylhydrazine hydrochloride 17.1 g (86%) was collected by filtration as a tan solid, m.p. 158°–165° C.

Step 4. Preparation of 4-[3-Chloro-2-(2,2,2-trifluoroethoxy)phenylhydrazono]-1-butanol The 3-chloro-2-(2,2,2-trifluoroethoxy)phenylhydrazine hydrochloride (13.3 g, 48 mmol) was dissolved in $H_2O$ (133 mL) and THF (133 mL). Dihydrofuran (3.75 mL, 48 mmol) was added in one portion, and the reaction mixture was stirred for 3 hours. After this time, the organic layer was separated and the aqueous layer extracted with $Et_2O$ (250 mL). The combined organic layers were washed with brine (250 mL), dried ($MgSO_4$), and concentrated to afford 14 g (98%) of a 3:1 mixture of E:Z isomers of 4-[3-chloro-2-(2,2,2-trifluoroethoxy)phenylhydrazono]-1-butanol as an orange oil which was used without further purification.

MS: m/e 310, 312 (17.0, 6.6, M+)

Step 5. Preparation of 6-Chloro-7-(2,2,2-trifluoroethoxy)tryptophol

A mixture of 4-[3-chloro-2-(2,2,2-trifluoroethoxy)-phenylhydrazono]-1-butanol (49 g, 150 mmol) and $ZnCl_2$ (48 g, 350 mmol) was heated to 150°–160° C. in 200 mL of ethylene glycol for 1 hour. The reaction mixture was then poured into 100 mL of 1N HCl and extracted with ether (3×400 mL). The combined ether extracts were washed first with $H_2O$ (150 mL) and then brine (1000 mL). The organic layer was dried ($MgSO_4$), concentrated, and the resulting residue was subjected to flash chromatography on a 6" column and eluted with 1:1 EtOAc:hexane. Concentration of pure fractions yielded 19 g (43%) of 6-chloro-7-(2,2,2-trifluoroethoxy)tryptophol.

$^1$H NMR ($CDCl_3$): δ 8.27 (bs, 1H), 7.35 (d, 1H, J=6 Hz), 7.13 (s, 1H), 7.10 (d, 1H, J=6 Hz), 4.58 (q, 2H, J=8 Hz), 3.90 (t, 2H, J=6 Hz), 3.01 (t, 2H, J=6 Hz),

Step 6. Preparation of Methyl 7-Chloro-1-ethyl-1,3,4,9-tetrahydro-8-(2,2,2-trifluoroethoxy)pyrano[3,4-b]indole-1-acetate 6-Chloro-7-(2,2,2-trifluoroethoxy)tryptophol (2.4 g, 8.2 mmol) and methyl 3-methoxy-2-propenoate (1.18 g, 9 mmol) were dissolved in 40 mL of methylene chloride. After the addition of $BF_3.Et_2O$ (0.2 mL), the reaction was stirred for 18 hours. At the end of this time, the solution was washed with saturated sodium bicarbonate (50 mL), and the methylene chloride layer separated, dried ($MgSO_4$) and concentrated to afford a brown oil. This residue was subjected to flash chromatography on a 2" column and eluted with methylene chloride. Concentration of the pure fractions yielded 3.2 g (97%) of methyl 7-chloro-1-ethyl-1,3,4,9-tetrahydro-8-(2,2,2-trifluoroethoxy)pyrano[3,4-b]indole-1-acetate.

NMR ($CDCl_3$): δ 9.30 (bs, 1H), 7.29 (d, 1H, J=8 Hz), 7.04 (d, 1H, J=8 Hz), 4.55 (m, 2H), 4.00 (m, 2H), 3.66 (s, 3H), 3.02 (d, 1H, J=17 Hz), 2.91 (d, 1H, J=17 Hz), 2.75 (m, 2H), 2.10 (m, 2H), 0.75 (t, 3H, J=8 Hz)

Step 7. Preparation of 7-Chloro-1-ethyl-1,3,4,9-tetrahydro-8-(2,2,2-trifluoroethoxy)-pyrano[3,4-b]indole-1-acetic Acid A mixture of methyl 7-chloro-1-ethyl-1,3,4,9-tetrahydro-8-(2,2,2-trifluoroethoxy)-pyrano[3,4-b]indole-1-acetate (3.2 g, 8 mmol) EtOH (25 mL) and 1N NaOH (10 mL) was refluxed for 2 hours. At the end of this time the EtOH was removed in vacuo and the rsidue diluted with $H_2O$ (25 mL). This aqueous mixture was acidified with 1N HCl, then extracted with ether (150 mL). The ether layer was washed with saturated brine (2×100 mL), dried ($MgSO_4$), and concentrated to yield a light yellow oil. This oil was dissolved in toluene and petroleum ether added (∼10 volumes). After cooling, the crystals were removed by filtration to yield 2.8 g (90%) of 7-chloro-1-ethyl-1,3,4,9-tetrahydro-8-(2,2,2-trifluoroethoxy)-pyrano[3,4-b]indole-1-acetic acid, m.p. 157° C.

EXAMPLE 6

1-Ethyl-1,3,4,9-tetrahydro-8-(2,2,2-trifluoroethoxy)-pyrano[3,4-b]indole-1-acetic Acid (I, $R^1$=—H, $R^2$=8—O—$CH_2$—$CF_3$)

Step 1. Preparation of 2-(2,2,2-Trifluoroethoxy)nitrobenzene

According to J. P. Idoux et al, *J. Org. Chem.* 48, 3771 (1983), to a stirred mixture of sodium hydride (12.3 g of 60% dispersion, 0.31 mol) in HMPA (350 mL) was added 2,2,2-trifluoroethanol (70 g, 0.7 mol) and stirring continued for 20 minutes. Then 2-chloronitrobenzene (48.3 g, 0.31 mol) was added and the reaction heated at 150°-155° C. for 3 hours. The reaction was cooled, poured into 5% HCl and extracted thrice with ether. The combined ether was washed with water, dried ($MgSO_4$), filtered and evaporated to give 68 g of oil. Distillation (98°-100° C., 3 mm Hg) afforded 51.0 g (74%) of 2-(2,2,2-trifluoroethoxy)nitrobenzene.

Step 2. Preparation of 2-(2,2,2-Trifluoroethoxy)aniline Hydrochloride 2-(2,2,2-Trifluoroethoxy)nitrobenzene (50 g, 0.226 mol) in 400 mL of ethanol containing 2.5 g of 10% palladium on carbon was hydrogenated in a shaking Parr bomb apparatus until $H_2$ uptake had ceased (approximately 3 hours). The reaction was filtered, diluted with ether, ethereal HCl added and the resulting precipitated solid collected and dried to give 45.0 g (87%) of 2-(2,2,2-trifluoroethoxy)aniline hydrochloride.

MS: m/e 191 (M)+, 80

Step 3. Preparation of 2-(2,2,2-Trifluoroethoxy)phenylhydrazine Hydrochloride Sodium nitrite (11.7 g, 0.17 mol) in 25 mL water was added dropwise to a cold stirred mixture of 2-(2,2,2-trifluoroethoxy)aniline hydrochloride (33.7 g, 0.15 mol), concentrated HCl (53 mL) and water (25 mL) so that the temperature remained at −5° to −3° C. After the additio was complete, a solution of stannous chloride dihydrate (71.7 g, 0.32 mol) in 122 mL 6N HCl was added over a 1 hour period. After 0.5 hour at 0° C. the reaction was allowed to warm to room temperature. Stirring was continued for 24 hours, the reaction diluted with water, ethyl acetate (400 mL) added, cooled and made alkaline using 50% NaOH. The phases were separated and the organic phase washed with water, dried ($MgSO_4$), filtered and concentrated to give an oil. The oil was dissolved in ether and treated with ethereal HCl. The resulting precipitated solid was collected and dried to give 26.4 g (73%) of 2-(2,2,2-trifluoroethoxy)phenylhydrazine hydrochloride, m.p. 168°-170° C.

Step 4. Preparation of 7-(2,2,2-Trifluoroethoxy)tryptophol 2,3-Dihydrofuran (13.4 g, 0.19 mol) was added dropwise to a stirred solution of 2-(2,2,2-trifluoroethoxy)phenylhydrazine hydrochloride (26.4 g, 0.109 mol) dioxane (110 mL), and water (6.6 mL). The reaction was heated at 95° C. for 3.5 hours, diluted with ether (1 liter) and decanted. The ethereal phase was dried ($MgSO_4$), filtered and concentrated to give 24 g of oil. Flash chromatography using 40% ethyl acetate in hexane afforded 7.3 g (26%) of the 7-(2,2,2-trifluoroethoxy)tryptophol, m.p. 82°-83° C.

Step 5. 1-Ethyl-1,3,4,9-tetrahydro-8-(2,2,2-trifluoroethoxy)-pyrano[3,4-b]indole-1-acetic Acid A mixture consisting of 7-(2,2,2-trifluoroethoxy)tryptophol (7.0 g, 0.027 mol) methyl 3-methoxy-3-propenoate (14.0 mL), dichloromethane (300 mL) and $BF_3.Et_2O$ (0.2 mL) was stirred at room temperature for 3 hours. The reaction was diluted with 200 mL of dichloromethane and washed with 5% $NaHCO_3$, and with water. The solution was dried ($MgSO_4$), filtered and concentrated to give 18.5 g of crude methyl 1-ethyl-1,3,4,9-tetrahydro-8-(2,2,2-trifluoroethoxy)pyrano[3,4-b]indole-1-acetate as an oil. This oil was dissolved in methanol (300 mL), containing KOH (11 g) and water (10 mL) and refluxed for 3 hours. The solution was concentrated, water added and washed twice with ether. The aqueous solution was acidified with 6N HCl, and extracted thrice with chloroform. The combined chloroform extracts were washed with water, dried ($MgSO_4$), filtered and concentrated to give 7.75 g of solid. Recrystallization from benzene-petroleum ether afforded 5.5 g (57% ) of pure 1-ethyl-1,3,4,9-tetrahydro-8-(2,2,2-trifluoroethoxy)-pyrano[3,4-b]indole-1-acetic acid, m.p. 126°-129° C.

EXAMPLE 8

1-Ethyl-1,3,4,9-tetrahydro-8-[(2-propynyl)oxy]-pyrano[3,4-b]indole-1-acetic Acid (I, $R^1$=—H, $R^2$=8—O—$CH_2$—C≡CH)

Step 1. Preparation of 3-Benzyloxy-2-nitrotoluene

A mixture of 3-methyl-2-nitrophenol (50 g, 0.326 mol), $K_2CO_3$ (45 g, 0.326 mol) and benzylbromide (61.4 g, 42.6 mL, 0.359 mol) in dry DMF (200 mL) was stirred at 90° C. for 3 hours under nitrogen. Most of the DMF was removed at reduced pressure and the residue was partitioned between water (300 mL) and ether (300 mL). The organic layer was washed with brine and dried ($Na_2SO_4$). Removal of the solvent provided (70 g, 88%) of 3-benzyloxy-2-nitrotoluene as an orange oil.

NMR (200 MHz, $CDCl_3$) δ 2.25 (s, 3H, $CH_3$), 5.15 (s, 2H, $OCH_2Ar$), 6.75-7.50 (m, 8H, Ar—H)

MS (m/z, EI) 243 (M)+, 91 (b.p.)

Step 2. Preparation of 1-[2-[2-Nitro-3-(phenylmethoxy)phenyl]ethenyl]pyrrolidine A solution of 3-benzyloxy-2-nitrotoluene (60 g, 247 mmol), N,N-dimethylformamide dimethylacetal (32 g, 36 mL, 270 mmol) and pyrrolidine (19.2 g, 22.5 mL, 270 mmol) in dry DMF (100 mL) was stirred at 110° C. under nitrogen for 3 hours. Removal of the solvent in vacuo yielded a crude material (red oil, 78.8 g) consisting of a mixture of 1-[2-[2-nitro-3-(phenylmethoxy)-phenyl]ethenyl]-pyrrolidine and N-methyl-N-[2-[2-nitro-3-(phenylmethoxy)phenyl]ethenyl]methan-amine together with some unreacted starting material. It was used immediately in the next step without further purification.

MS (m/z, EI) 324 (M)+, 91 (b.p.)

Step 3. Preparation of 7-Benzyloxyindole

Hydrazine hydrate (4.6 g, 92 mmol, 85% solution) was added to a mechanically stirred mixture of 1-[2-[2-nitro-3-(phenylmethoxy)phenyl]ethenyl]pyrrolidine and N-methyl-N-[2-[2-nitro-3-(phenylmethoxy)phenyl]ethenyl]methanamine (20 g, 61.8 mmol, crude product obtained as described in Step 2) and Raney-Nickel (5 g) in methanol (500 mL), care being taken to keep the temperature at 45°-50° C. Two additional portions of hydrazine hydrate (4.6 g each ) were added after 30 and 60 minutes, respectively. The temperature was maintained at 45°-50° C. for 5 hours. After stirring overnight at room temperature, the mixture was filtered off (Celite) and the filtrate was concentrated in vacuo. The residue (dark liquid) was purified by flash-chromatography (on silica Merck-60, dichloromethane-light petroleum ether 1:1) to yield pure 7-benzyloxyindole as an oil that solidifies upon standing (2.3-3.03 g, 17-22%, based upon different runs). A sample was recrystallized from petroleum ether as white needles, m.p. 62°-63° C. (Dictionary of Organic Compounds Vol III, p 3077, m.p. 67°-68° C., ligroin).

NMR (400 MHz, CDCl$_3$) δ 5.20 (s, 2H, OCH$_2$Ar), 6.53 (t, J=ca. 3 Hz, 1H, Ar—H), 6.71 (d, J=8 Hz, 1H, Ar—H), 7.01 (t, J=8 Hz, 1H, Ar—H), 7.16 (t, J=ca. 3 Hz, 1H, Ar—H), 7.26 (d, J=8 Hz, 1H, Ar—H), 7.3-7.5 (m, 5H, Ar—H)

Step 4. Preparation of Ethyl 7-(Phenylmethoxy)-indol-3-yl-glyoxylate

Oxalyl chloride (3.2 g, 2.2 mL, 24.7 mmol) was added dropwise under nitrogen to an ice cold solution of ethyl 7-(phenylmethoxy)-indole (2.3 g, 10.3 mmol) in anhydrous ether (40 mL). The mixture was stirred for 1 hour at room temperature during which time a yellow precipitate was formed. The solvent and the excess of oxalyl chloride was removed at reduced pressure to yield 7-(phenylmethoxy)-indol-3-yl-glyoxyl chloride. Ethanol (50 mL) was then added to the residue and the solution was stirred overnight under nitrogen at room temperature. Removal of the solvent in vacuo provided ethyl 7-(phenylmethoxy)-indol-3-yl-glyoxylate as a tan solid (3 g, 94%).

NMR (200 MHz, CDCl$_3$) δ 1.45 (t, 3H, CH$_2$CH$_3$), 4.40 (q, 2H, OCH$_2$CH$_3$), 5.21 (s, 2H, CH$_2$Ar), 6.8 (d, 1H, Ar—H), 7.25 (t, 1H, Ar—H), 7.45 (m, 5H, Ar—H), 8.05 (d, 1H, Ar—H), 8.4 (d, 1H, Ar—H), 9.05 (broad, 1H, NH)

Step 5. Preparation of 7-(Phenylmethoxy)-tryptophol

A stirred solution of ethyl 7-(phenylmethoxy)-indol-3-yl-glyoxylate (3 g, 9.3 mmol) indry THF (100 mL) was treated portionwise under nitrogen with LAH (0.76 g, 20 mmol). The mixture was refluxed for 4 hours, cooled and treated sequentially with water (0.75 mL), 1N—NaOH (0.75 mL), water (2.25 mL) and sodium sulfate (9.5 g). The mixture was stirred for 10 minutes, filtered (Celite) and the cake thoroughly washed with ether. The combined filtrate and washings were evaporated to dryness to provide 7-(phenylmethoxy)-tryptophol as a light pink solid (2.4 g, 100%), m.p. 60°-62° C.

NMR (400 MHz, CDCl$_3$) δ 1.6 (1H, OH), 3.01 (t, J=6.2 Hz, 2H, ArCH$_2$), 3.9 (t, J=6.1 Hz, 2H, CCH$_2$O), 5.2 (s, 2H, OCH$_2$Ar), 6.73 (d, J=7.6 Hz, 1H, Ar—H), 7.03 (t, 1H, Ar—H), 7.24 (d, J=8.3 Hz, 1H, Ar—H), 7.34-7.52 (m, 5H, Ar—H), 8.31 (broad, 1H, NH)

Anal. Calcd. for C$_{17}$H$_{17}$NO$_2$: C, 76.38; H, 6.41; N, 5.24% Found: C, 76.36; H, 6.29; N, 5.50%

Step 6. Preparation of Methyl 1-Ethyl-1,3,4,9-tetrahydro-8-(phenylmethoxy)-pyrano[3,4-b]indole-1-acetate A solution of 7-(phenylmethoxy)-tryptophol (2.4 g, 9 mmol), methyl 3-methoxy-2-pentenoate (1.95 g, 13.5 mmol) and a catalytic amount of boron trifluoride etherate in dry CH$_2$Cl$_2$ (40 mL) was stirred at room temperature under nitrogen for 1 hour. The reaction mixture was washed with 10% NaHCO$_3$ solution (30 mL) and brine (20 mL) and dried (MgSO$_4$). Removal of the solvent left a dark oil (3.4 g, 100%) which was used as such in the next step.

NMR (200 Mz, CDCl$_3$) δ 0.81 (t, J=7.8 Hz, 3H, CH$_2$CH$_3$), 2.05 (m, 2H, CH$_2$CH$_3$), 2.8 (m, 2H, ArCH$_2$), 2.94 (d, 2H, CH$_2$CO$_2$), 3.7 (s, 3H, OCH$_3$), 4.0 (m, 2H, CCH$_2$O), 5.24 (s, 2H, OCH$_2$Ar), 6.69 (d, J=7.3 Hz, 1H, Ar—H), 6.99 (t, J=7.8 Hz, 1H, Ar—H), 7.13 (d, J=8 Hz, 1H, Ar—H), 7.3-7.5 (m, 5H, Ar—H), 8.93 (1H, NH)

Step 7. Preparation of Methyl 1-Ethyl-1,3,4,9-tetrahydro-8-hydroxy-pyrano[3,4-b]indole-1-acetate According to the procedure of A. F. Felix et al, J. Org. Chem., 43, 4194 (1978), a mixture of methyl 1-ethyl-1,3,4,9-tetrahydro-8-(phenylmethoxy)pyrano[3,4-b]indole-1-acetate (1 g, 2.6 mmol), cyclohexene (2.13 g, 2.6 mL, 2.56 mmol) and 10% Pd/C in methanol (15 mL) was refluxed for 1 hour. The catalyst was filtered off (Solka-Floc) and the filtrate evaporated to dryness to provide mthyl 1-ethyl-1,3,4,9-tetrahydro-8-hydroxy-pyrano[3,4-b]indole-1-acetate as a foam (0.68 g, 90.6%)

NMR (200 MHz, CDCl$_3$) δ 0.82 (t, J=7.3 Hz, 3H, CH$_2$CH$_3$), 2.05 (m, 2H, CH$_2$CH$_3$), 2.78 (m, 2H, ArCH$_2$), 2.95 (d, 2H, CH$_2$CO$_2$), 3.70 (s, 3H, OCH$_3$), 4.0 (m, 2H, CCH$_2$O), 5.03 (broad, 1H, OH), 6.6 (d, 1H, Ar—H), 6.95 (t, 1H, Ar—H), 7.10 (d, 1H, Ar—H), 9.0 (1H, NH)

MS (m/z, EI) 289 (M)+, 216 (M—CH$_2$CO$_2$CH$_3$, b.p.)+

Step 8. Preparation of Methyl 1-Ethyl-1,3,4,9-tetrahydro-8-[(2-propynyl)oxy]-pyrano[3,4-b]indole-1-acetate A mixture of methyl 1-ethyl-1,3,4,9-tetrahydro-8-hydroxy-pyrano[3,4-b]indole-1-acetate (6 g, 20.8 mmol), 3-bromo-1-trimethylsilyl-1-propyne [4.8 g, 25 mmol, prepared according to R. B. Miller, Synth. Comm., 2, 267 (1972)] and 2.5N—NaOH (10 mL, 25 mmol) in DMSO (60 mL) was heated under nitrogen for 30 minutes at 120° C. Upon cooling, the micture was diluted with 2 volumes of water, acidified with 2N—KHSO$_4$ solution and extracted with ether. The extracts were dried (Na$_2$SO$_4$) and concentrated in vacuo. The residual oil (7 g) was flash-chromatographed (silica Merck-60, chloroform) to provide methyl 1-ethyl-1,3,4,9-tetrahydro-8-[(2-propynyl)oxy]-pyrano[3,4-b]indole-1-acetate (5.6 g, 83%) as an oil.

NMR (400 MHz, CDCl$_3$) δ 0.8 (t, J=7.3 Hz, 3H, CH$_2$CH$_3$), 2.04 and 2.14 (mm, 2H, CH$_2$CH$_3$), 2.53 (t, J=2.36 Hz, 1H, C≡CH), 2.70-2.82 (m, 2H, ArCH$_2$), 2.93 (dd, 2H, CH$_2$CO$_2$), 3.70 (s, 3H, OCH$_3$), 3.94 and 4.03 (mm, 2H, CCH$_2$O), 4.84 (s, 2H, OCH$_2$C≡C), 6.75 (d, J=7.8 Hz, 1H, Ar—H), 7.01 (t, J=7.8 Hz, 1H, Ar—H), 7.15 (d, J=7.9 Hz, 1H, Ar—H), 8.98 (s, 1H, NH)

MS (m/z, EI) 327 (M)$^+$, 298 (M—C$_2$H$_5$)$^+$, 254, 83 (b.p.)

Step 9. Preparation of 1-Ethyl-1,3,4,9-tetrahydro-8-[(2-propynyl)oxy]-pyrano[3,4-b]indole-1-acetic Acid A solution of methyl 1-ethyl-1,3,4,9-tetrahydro-8-[(2-propynyl)oxy]pyrano[3,4-b]indole-1-acetate (2 g, 6.1 mmol), in ethanol (10 mL) was treated with 2.5N—NaOH (10 mL) and stirred overnight under nitrogen at room temperature. The ethanol was removed and the residue acidified in the cold with 2N—HCl and extracted with ether. The extracts were washed with brine and dried (Na$_2$SO$_4$). The solvent was evaporated and the residue recrystallized from ether-hexane to provide the product as a buff-colored solid (1.05 g, 55.3%), m.p. 155°-156° C. (dec.).

UV (MeOH, nm) 268.5 (ε 8,200)

NMR (400 MHz, CDCl$_3$) δ 0.85 (t, J=7.3 Hz, 3H, CH$_2$CH$_3$), 2.06 (m, 2H, CH$_2$CH$_3$), 3.53 (t, J=2.4 Hz, 1H, C≡CH), 2.83 (m, 2H, ArCH$_2$), 3.0 (d, 2H, CH$_2$CO$_2$), 4.02-4.14 (m, 2H, CCH$_2$O), 4.8 (d, 2H, CH$_2$C≡C), 6.74 (d, J=7.8 Hz, 1H, Ar—H), 7.02 (t, J=7.8 Hz, 1H, Ar—H), 7.15 (d, J=7.8 Hz, Ar—H), 8.7 (s, 1H, NH)

MS (m/z, DCI) 314 (M+H)$^+$, 275 (M—CH$_2$C≡CH)$^+$, 254, 216 (b.p.)

Anal. Calcd. for C$_{18}$H$_{19}$NO$_4$: C, 68.99; H, 6.11; N, 4.47% Found: C, 69.19; H, 5.91; N, 4.29%

TABLE II

Substituted 1,3,4,9-Tetrahydropyrano[3,4-b]indole-1-acetic Acids

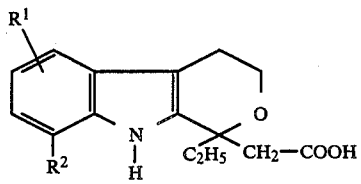

| Example | R$^1$ | R$^2$ | Melting Point °C. |
|---|---|---|---|
| 1 | 5-CH$_3$ | —O—CH$_2$—CF$_3$ | 149–151 |
| 2 | 7-Cl | —O—CH$_2$—CF$_3$ | 155–157 |
| 3 | 5-F | —O—CH$_2$—CF$_3$ | 148–150 |
| 4 | 7-F | —O—CH$_2$—CF$_3$ | 152–154 |
| 5 | 7-Cl | —O—CH(CH$_3$)—CF$_3$ | 119–126 |
| 6 | —H | —O—CH$_2$—CF$_3$ | 126–129 |
| 7 | —H | —O—CH$_2$—CH=CH$_2$ | 148–150 |
| 8 | —H | —O—CH$_2$—C≡CH | 155–156 |

We claim:

1. The compounds having the structure

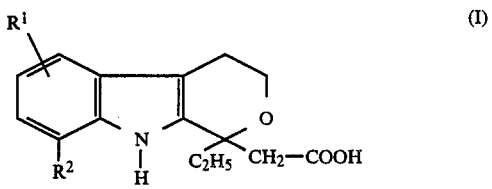

(I)

wherein R$^1$ is hydrogen, lower alkyl containing 1 to 4 carbon atoms or halogen, R$^2$ is —O—CH$_2$—CH=CH$_2$, —O—CH$_2$—CF$_3$, —O—CH(CH$_3$)—CF$_3$, —O—CH$_2$—C≡CH and the pharmaceutically acceptable salts thereof.

2. The compounds according to claim 1 wherein R$^1$ is hydrogen or chlorine, R$^2$ is —O—CH$_2$—CF$_3$ and the pharmaceutically acceptable salts thereof.

3. The compound according to claim 2 designated 7-chloro-1-ethyl-1,3,4,9-tetrahydro-8-(2,2,2-trifluoroethoxy)-pyrano[3,4-b]indole-1-acetic acid and the pharmaceutically acceptable salts thereof.

4. A compound according to claim 2 designated 1-ethyl-1,3,4,9-tetrahydro-8-(2,2,2-trifluoroethoxy)-pyrano[3,4-b]indole-1-acetic and the pharmaceutically acceptable salts thereof.

5. A pharmaceutical composition comprising a compound of structure (I), or a pharmaceutically acceptable salt thereof, as define in claim 1 and a pharmaceutically acceptable carrier.

6. A pharmaceutical composition comprising a compound of structure (I), or a pharmaceutically acceptable salt thereof, as defined in claim 1, a nonsteroid anti-inflammatory drug selected from the group consisting of, ibuprofen and aspirin, an opiate analgesic selected from the group consisting of codeine, oxycodone and morphine and a pharmaceutically acceptable carrier.

7. A method for treating inflammatory conditions and for analgesic purposes in conditions which require relief from pain in a mammal which comprises the administration to said mammal of an effective amount of a compound selected from those of formula (I), or a pharmaceutically acceptable salt thereof, as claimed in claim 1.

8. A method for treating inflammatory conditions and for analgesic purposes in conditions which require relief from pain in a mammal which comprises the administration to said mammal of an effective amount of a compound selected from those of formula (I), or a pharmaceutically acceptable salt thereof, as claimed in claim 1, in conjunction with nonsteroid anti-inflammatory drugs and opiate analgesics.

* * * * *